(12) United States Patent
Ramirez et al.

(10) Patent No.: US 9,622,429 B2
(45) Date of Patent: Apr. 18, 2017

(54) METHOD FOR INCREASING PLANT BIOMASS

(75) Inventors: Alfredo Martinez Ramirez, La Rioja (ES); Jorge Conrado Arenas Vidal, La Rioja (ES)

(73) Assignee: BioMass Booster, S.L., La Rioja (ES)

( * ) Notice: Subject to any disclaimer, the term of this patent is extended or adjusted under 35 U.S.C. 154(b) by 483 days.

(21) Appl. No.: 13/699,706

(22) PCT Filed: May 24, 2011

(86) PCT No.: PCT/EP2011/058464
§ 371 (c)(1),
(2), (4) Date: Apr. 17, 2013

(87) PCT Pub. No.: WO2011/147826
PCT Pub. Date: Dec. 1, 2011

(65) Prior Publication Data
US 2013/0205451 A1    Aug. 8, 2013

(30) Foreign Application Priority Data

May 25, 2010 (EP) ..................................... 10382143

(51) Int. Cl.
| | |
|---|---|
| *A01H 3/04* | (2006.01) |
| *C12N 1/12* | (2006.01) |
| *A01H 4/00* | (2006.01) |
| *A01N 63/00* | (2006.01) |
| *C07K 14/415* | (2006.01) |

(Continued)

(52) U.S. Cl.
CPC ............... *A01H 3/04* (2013.01); *A01H 4/001* (2013.01); *A01N 63/00* (2013.01); *A01N 65/08* (2013.01); *A01N 65/44* (2013.01); *C07K 14/415* (2013.01); *C07K 14/435* (2013.01); *C07K 14/575* (2013.01); *C12N 1/12* (2013.01);

(Continued)

(58) Field of Classification Search
CPC ..................................... A01H 3/04; C12N 1/12
See application file for complete search history.

(56) References Cited

U.S. PATENT DOCUMENTS 6,320,022 B1 * 11/2001 Cutitta et al. ................. 530/300
2002/0168392 A1 * 11/2002 Manners et al. .............. 424/405

(Continued)

FOREIGN PATENT DOCUMENTS

| WO | WO-2004035798 | 4/2004 |
|---|---|---|
| WO | WO-2010046221 | 4/2010 |
| WO | WO-2011044254 | 4/2011 |

OTHER PUBLICATIONS

Ouafik, L'Houcine, et al. "Neutralization of adrenomedullin inhibits the growth of human glioblastoma cell lines in vitro and suppresses tumor xenograft growth in vivo." The American Journal of Pathology 160.4 (2002): 1279-1292.*

(Continued)

*Primary Examiner* — Amjad Abraham
*Assistant Examiner* — Fan Weihua
(74) *Attorney, Agent, or Firm* — Blakely Sokoloff Taylor & Zafman LLP

(57) ABSTRACT

The invention relates to the use of a peptide comprising a six-member ring created by the disulfide bond between two cysteines in the increase of biomass of a photosynthetic organism, for its application in the wood industry, in obtaining energy coming from renewable sources and in agriculture.

10 Claims, 2 Drawing Sheets

(51) Int. Cl.
| | |
|---|---|
| C07K 14/435 | (2006.01) |
| C07K 14/575 | (2006.01) |
| C12N 5/00 | (2006.01) |
| C12N 15/82 | (2006.01) |
| A01N 65/08 | (2009.01) |
| A01N 65/44 | (2009.01) |

(52) U.S. Cl.
CPC ....... *C12N 5/0025* (2013.01); *C12N 15/8257* (2013.01); *C12N 15/8261* (2013.01)

(56) References Cited

U.S. PATENT DOCUMENTS

| | | |
|---|---|---|
| 2006/0235213 A1 | 10/2006 | Alexandrov et al. |
| 2008/0127365 A1* | 5/2008 | Sanz Molinero et al. .... 800/278 |
| 2008/0148432 A1* | 6/2008 | Abad ............................ 800/279 |

OTHER PUBLICATIONS

Murashige, Toshio, and Folke Skoog. "A revised medium for rapid growth and bio assays with tobacco tissue cultures." *Physiologia plantarum* 15.3 (1962): 473-497.*

Ouflik, L.H., et al., 2002, The American Journal of Pathology 160(4): 1279-1292.*

Murashige, T., and Skoog, F., 1962, A revised medium for rapid growth and bio assays with tobacco tissue cultures. *Physiologia plantarum* 15(3): 473-497.*

Kato, Ryoichi, et al. "Effects of an epidermal growth factor on growth of *Zea* primary roots and mesocotyls." Plant and cell physiology 36.1 (1995): 197-199.*

PCT Search Report; PCT/EP2011/058464 dated Jul. 28, 2011.

Database UniProt; Mar. 2, 2010; XP002599053; Database accession No. P43145; the whole document.

Database Uniprot; Feb. 2, 2010; XP002599054; Database accession No. Q84RF4; the whole document.

Database UniProt; Apr. 20, 2010; XP002599055; Database accession No. Q9XF50; the whole document.

Giannino, Donato, et al., "The overexpression of asparagine synthetase A from *E. coli* affects the nitrogen status in leaves of lettuce (*Lactuca sativa* L.) and enhances vegative growth", *Euphytica*, Kluwer Academic Publishers, DO, vol. 162, No. 1, Aug. 9, 2007, pp. 11-22.

Gorr, Sven-Ulrik, "Antimicrobial peptides of the oral cavity", *Periodontology 2000 2009*; vol. 51; pp. 152-180; ISSN: 1600-0757; p. 154, col. 2, line 9- line 25, table 4A.

Suzuki, Nobuhiro, et al., "Enhanced Tolerance to Environmental Stress in Transgenic Plants Expressing the Transcriptional Coactivator Multiprotein Bridging Factor 1c 1(W)", *Plant Physiology, American Society of Plant Physiologists*, Rockville, MD; vol. 139, No. 3; Nov. 1, 2005; pp. 1313-1322.

Capatina, C., et al., "Acromegaly", *Journal of Endocrinology*, vol. 226, No. 2, (2015), T141-T160.

Yang, F., et al., "An auxin-responsive endogenous peptide regulates root development in *Arabidopsis*", *Journal of Integrative Plant Biology*, vol. 56, No. 7, (Jul. 2014), 635-647.

* cited by examiner

METHOD FOR INCREASING PLANT BIOMASS

CROSS-REFERENCE TO RELATED APPLICATION

The application is a non-provisional application claiming the benefit of International Patent Application No. PCT/EP2011/058464, filed May 24, 2011, and incorporated herein by reference.

FIELD OF THE INVENTION

The present invention is comprised in the field of biotechnology, specifically, in the production of plant biomass. The present invention thus relates to the use of a peptide comprising a six-member ring created by the disulfide bond between two cysteines in the increase of the plant biomass, which has an application in the wood industry, in obtaining energy coming from renewable sources and in agriculture.

BACKGROUND OF THE INVENTION

Cell growth both in plants and in animals, is orchestrated by a series of extracellular signals known as hormones or growth factors (Galinha et al. 2009, Semin Cell Dev Biol. 20: 1149-1156), which act through specific membrane receptors (Santner and Estelle 2009, Nature 459: 1071-1078; De, I et al. 2009, Nat Cell Biol 11: 1166-1173). These hormones can be synthesized within the plant or they can come from external organisms, as is the case of the factors produced by rhizobacteria which favor the growth of their symbiont plant (Lugtenberg and Kamilova 2009, Annu Rev Microbiol 63:541-556).

Five groups of growth factors in plants have been established: auxins, gibberellins, cytokinins, abscisic acid and its derivatives and ethylene. These substances are widely distributed and can, in fact, be found in all higher plants. They are specific in terms of their action, perform their activity at very low concentrations, and regulate cell growth, cell division and differentiation, as well as organogenesis, the senescence and the latency state. Less frequent though not entirely unknown, is the case in which a conservation of the structure of a growth factor occurs in such a way that said growth factor is functional both in plants and in animals. A typical example is the glycoprotein known as granulin, having representatives from fungi to mammals, and performing functions as varied as modulation of the vegetative growth in vegetables, or the regulation of cancer in animals (Bateman and Bennett 2009, Bioessays 31: 1245-1254).

For the purpose of regulating the development of plants and increasing plant biomass, a number of attempts to control the growth thereof by means of using chemical compounds have been made, such as, for example, that described in patent application EP0934951A1, or fertilizers. Patent application US2010/0016166A1 describes a method for increasing the number of seeds and flowers of a plant which comprises cultivating a plant in the presence of glutamate. International patent application WO2010/001184A1 describes a composition comprising (i) a micronized natural calcite mineral; (ii) micronized zeolite; and (iii) one or more additives for stimulating plant growth and improving the crop yield. However, mineral fertilization has a negative effect on agricultural production because the high concentrations of fertilizer can damage the soil and the desired results in terms of crop yield are not always obtained.

In recent years, and due to the advances in genetic manipulation, a new strategy has been developed for increasing the plant biomass consisting of controlling the expression of determined genes which control cell metabolism of the plant. In this sense, US patent application US2009/0094716A1 describes a method for increasing the plant biomass comprising the manipulation of the expression of the fve gene encoding a protein (FEV) having 6 copies of a WD40 domain. The inhibition of the expression of FVE provides the plant with an improved agricultural property, specifically, the increase in the yield of the biomass produced by the plant with respect to a control plant. In addition, international patent application WO2007/027866 describes the use of a recombinant DNA for the expression of proteins useful in controlling plant morphology, physiology and growth. Said recombinant DNA comprises a functional promoter in plants covalently bound to a nucleotide sequence encoding a protein which has at least one domain of the Pfam family of proteins. Patent application WO2009/003429A2 describes a method for regulating the biomass production in plants comprising the modification of the expression of the cki1 gene or of orthologs or homologs thereof. US patent application US2010/0037351A1 describes the increase of plant biomass, and with it the yield of the plant under hyperosmotic stress by means of the overexpression in the plants of the gene encoding the phospholipase Dε (PLDε). Nevertheless, the methods involving genetic manipulation of the plant are usually expensive and are not accepted by society.

International patent application WO2004/035798 discloses the identification of genes that are upregulated or downregulated in transgenic plants overexpressing E2Fa/DPa and the use thereof to alter plant characteristics; in particular, the protein of SEQ ID NO: 1848 is disclosed although its eventual use as plant growth factor is not shown.

Further, international patent application WO2004/035798 discloses, in general, a method for producing a plant with increased yield as compared to a corresponding wild type plant comprising at least increasing the activities of a group of proteins, including the proteins of SEQ ID NO: 4659 and 4660, although the ability of said proteins to increase plant biomass is not disclosed.

Therefore, there is a need in the state of the art to develop alternative methods to those already existing for increasing the plant biomass and with it, the crop yield, which do not have the aforementioned drawbacks.

It has now been found that the administration of adrenomedullin to plants and algae increases their biomass. Adrenomedullin (AM) and the peptide of 20 amino acids of the N-terminal region of proadrenomedullin (PAMP) come from post-translational processing of the same protein, pre-proadrenomedullin, which is encoded by the adm gene. Despite not having any structural similarity, both peptides produce similar and a large number of physiological responses. Among these are their vasodilator effect, bronchodilator effect, cell motility and growth regulator effect, modulator effect for the secretion of other hormones and intestinal absorption regulatory effect (López, J and Martínez, A. 2002. Int Rev Cytol 221: 1-92). In the context of cancer cells, AM acts like a growth factor, promotes cell motility, reduces apoptosis and induces angiogenesis (Martínez et al. 2002, J Natl Cancer Inst 94: 1226-1237).

SUMMARY OF THE INVENTION

The authors of the present invention have discovered that, surprisingly, the administration of adrenomedullin to plants and algae (including microalgae), in general, "photosynthetic organisms", produces in said organims growth of their biomass, thus discovering a new application for said protein as a growth factor in plants and algae.

As it is shown in Example 1, carrot and tobacco calli were placed in the presence of increasing concentrations of adrenomedullin and it was observed that in comparison with the control sample, an increase of growth in the calli occurred following a dose-dependent response (FIG. 1). Further, Example 2 shows that microalgae (*Chlorella*) treated with adrenomedullin grows up faster than the non-treated microalgae.

Therefore, based on these discoveries, the present invention allows increasing the plant biomass of a plant, or an alga, without having to apply hormones (gibberellins, auxins, cytokinins, etc.) or agrochemical products. Furthermore, given that it is a factor extrinsic to the photosynthetic organism (i.e., it is not produced naturally by plants or algae) it would not have side effects in the plant physiology (sap flow, stomata opening, turgidity, relations with symbiont fungi, etc.) or alga physiology and would only affect plant or alga growth, which is the effect that has been observed. Additionally, the fact that it is not produced naturally in plants or algae facilitates environmental controls and controls of genetically modified material spreading.

On the other hand, it is known that adrenomedullin has a characteristic motif (or identifying feature) in its amino acid sequence which is involved in receptor recognition, consisting of a 6 amino acid ring created by the disulfide bond between two cysteines [Cys-$Xaa_1$-$Xaa_2$-$Xaa_3$-$Xaa_4$-Cys]. Therefore, without wishing to be bound by any theory, it is believed that any protein having said motif in its amino acid sequence will recognize the receptor and trigger the processes which lead to an increase of the biomass of said photosynthetic organisms (e.g., plants or algae), performing its role as a growth factor.

Thus, based on this new effect of adrenomedullin on photosynthetic organisms (e.g., plants and algae), and taking into account the motif present in its amino acid sequence, the following inventive aspects have been developed:

A method for increasing the biomass of a photosynthetic organism, e.g., a plant or an alga, which comprises cultivating said photosynthetic organism in the presence of a peptide comprising:
(i) the amino acid sequence

[SEQ ID NO: 1]
Cys-$Xaa_1$-$Xaa_2$-$Xaa_3$-$Xaa_4$-Cys wherein $Xaa_1$, $Xaa_2$, $Xaa_3$ and $Xaa_4$ independently represent an amino acid, and
(ii) the cysteine residues of the amino acid sequence shown in (i) form a disulfide bridge between them.

A gene construct comprising:
(a) a nucleic acid encoding a peptide which comprises
(i) the amino acid sequence

[SEQ ID NO: 1]
Cys-$Xaa_1$-$Xaa_2$-$Xaa_3$-$Xaa_4$-Cys wherein $Xaa_1$, $Xaa_2$, $Xaa_3$ and $Xaa_4$ independently represent an amino acid and
(ii) the cysteine residues of the amino acid sequence shown in (i) form a disulfide bridge between them, and (b) regulating elements for regulating its expression in a photosynthetic organism.

A vector, a host cell, a transgenic photosynthetic organism cell, and a transgenic photosynthetic organism, e.g., a plant or an alga, comprising a gene construct such as the one defined above, or a nucleic acid encoding a peptide which comprises (i) the amino acid sequence Cys-$Xaa_1$-$Xaa_2$-$Xaa_3$-$Xaa_4$-Cys [SEQ ID NO: 1], wherein $Xaa_1$, $Xaa_2$, $Xaa_3$ and $Xaa_4$ independently represent an amino acid, and (ii) the cysteine residues of the amino acid sequence shown in (i) form a disulfide bridge between them.

These inventive aspects as well as the different particular embodiments thereof will be explained in detail below in the detailed description of the invention.

DETAILED DESCRIPTION OF THE INVENTION

Method of the Invention

Figure 1:
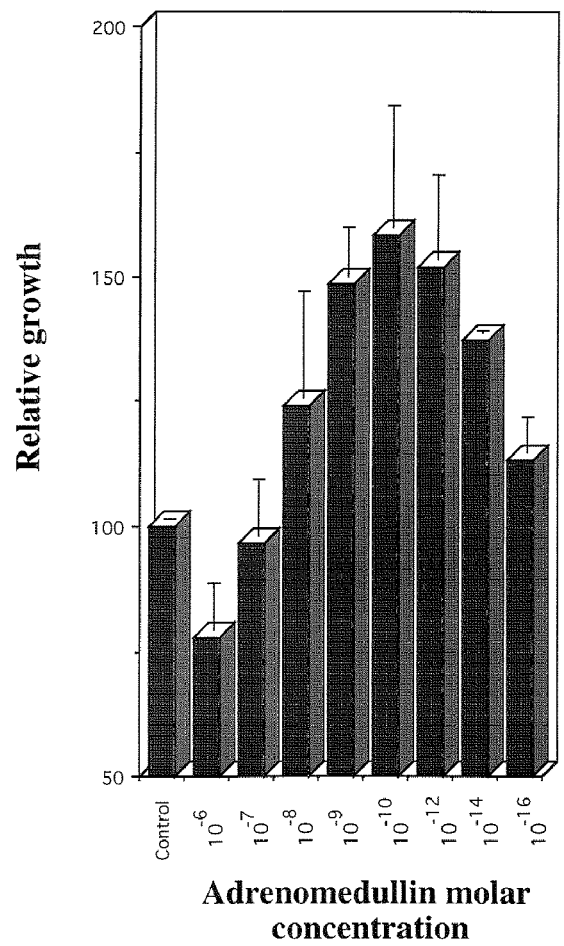
FIG. 1 is a bar chart showing the relative growth of the plant biomass depending on the molar concentration of adrenomedullin present in the medium. Each bar represents the statistical mean and the standard deviation of 8 independent repetitions.
Figure 2:
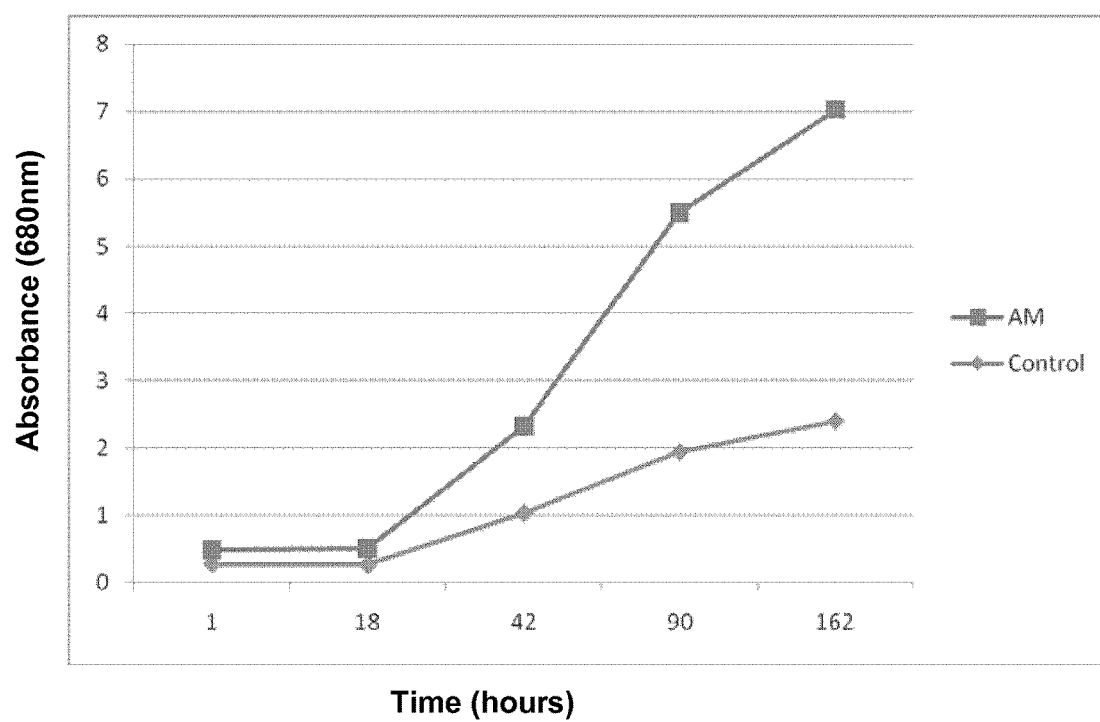
FIG. 2 is a graph showing the adrenomedullin effect over a microalgae (*Chlorella*); microalgae treated with adrenomedullin grows up faster than the non-treated microalgae.

In an aspect, the invention relates to a method for increasing the biomass of a photosynthetic organism (hereinafter referred to as method of the invention) which comprises cultivating said photosynthetic organism in the presence of a peptide (hereinafter referred to as growth factor of the invention) comprising:
(i) the amino acid sequence

[SEQ ID NO: 1]
Cys-$Xaa_1$-$Xaa_2$-$Xaa_3$-$Xaa_4$-Cys wherein $Xaa_1$, $Xaa_2$, $Xaa_3$ and $Xaa_4$ independently represent an amino acid, and
(ii) the cysteine residues of the amino acid sequence shown in (i) form a disulfide bridge between them.

The amino acids $Xaa_1$, $Xaa_2$, $Xaa_3$ and $Xaa_4$ can be identical to or different from one another. In a particular embodiment, $Xaa_1$, $Xaa_2$, $Xaa_3$ and/or $Xaa_4$ is an amino acid different from Cys.

As used herein, the term "photosynthetic organism" includes any organism capable of performing photosynthesis, i.e., a process that converts carbon dioxide into organic compounds, especially sugars, using the energy from sunlight. Photosynthesis occurs in plants, algae, and many species of bacteria, e.g., cyanobacteria, etc., but not in archaea. Photosynthetic organisms are also called photoautotrophs, since they can create their own food.

The term "plant", as used herein, includes living organisms belonging to the kingdom Plantae, e.g., trees, flowers, herbs, bushes, grasses, vines, ferns, mosses, green algae, etc. Currently, plants can be classified in three groups, namely: (i) Land plants or embryophytes, more formally Embryophyta or Metaphyta, which constitute the most familiar group of plants and include non-vascular land plants or briophytes, vascular plants or tracheophytes, which include seed plants or spermatopphytes; (ii) Green plants— also known as Viridiplantae, Viridiphyta or Chlorobiont; and (iii) Archaeplastida, Plastida or Primoplantae.

As used herein, the term "alga" includes a large and diverse group of simple, typically autotrophic organisms, ranging from unicellular to multicellular forms. In a particular embodiment, the alga is a microalga, i.e., a microscopic alga, typically found in freshwater and marine systems.

The term "cyanobacteria", commonly referred to as blue-green algae, as used herein, although was traditionally included as alga in older textbooks, many modern sources regard this as outdated as they are now considered to be bacteria.

In the context of the present invention, "biomass of a photosynthetic organism" is understood both the amount of biological material or organic matter which constitutes a photosynthetic organism, and the biological material or organic matter generated in a biological process, spontaneous or not spontaneous (i.e., provoked). In an embodiment, biomass is useable as an energy source, for example, wood, waste, (hydrogen) gas, alcohol fuels, etc.

In an embodiment, wherein the photosynthetic organism is a vascular plant, the biomass of said plant includes the amount of biological material or organic matter present in the plant, i.e., the biological material or organic matter constituting both the aerial part of the plant, i.e., the stem, the trunk, the leaves, the branches, the fruit, the flower heads, etc. (aerial biomass), and the underground part thereof, i.e., the roots, calli, tubers, etc. (underground biomass). The "plant biomass" is often measured as the dry mass or weight (or "fresh weight" where appropriate) of the plant.

In the present invention, the expression "increasing the biomass of a photosynthetic organism" is understood as the effect on the photosynthetic organism of obtaining a growth rate greater than 1, wherein the growth rate (GR) is defined by the formula:

GR=Final weight/initial weight

Another way of measuring an increase in the biomass of a photosynthetic organism is based on the calculation of the relative growth rate (RGR) or biomass gain per unit of biomass and time, and is defined by the formula:

RGR=$(LnW_2-LnW_1)/(t_1-t_2)$ wherein $W_1$ and $W_2$ are the weight of the plant in the times 2 and 1 ($t_2$-$t_1$ respectively) [Valladares, F. 2004, Ecología del bosque mediterráneo en un mundo cambiante, pp. 191-227. *Ministerio de Medio Ambiente* (Ministry of the Environment), EGRAF, S. A., Madrid].

As the person skilled in the art will understand, in the case of vascular plants, there are other parameters in the state of the art which, directly or indirectly related to the GR, can be used to determine the growth of the plant biomass of said plant. Illustrative, non-limiting examples of said parameters include:

the leaf area ratio (LAR) or leaf area to total plant weight ratio. It is expressed in $m^2$ (leaf) $kg^{-1}$ (plant). The leaf area can be measured by several methods. There are automatic leaf area measuring devices provided with a video camera, digital card and computer image analysis software which allow fairly quick area measurements (in addition to other dimensions: width, length, etc.) of a number of leaves. Another system is to photocopy or scan the leaves and by means of an image analysis software, estimating the surface. Another simple alternative is to cut out the silhouettes of the photocopied leaves and weigh them, using a cut-out of the same paper with a known surface to calibrate the weight/area ratio. Once the surface of the leaves is measured, the leaves are stored in paper envelopes with their identification, are dried in an oven and weighed to thus obtain the "dry weight";

the specific leaf area (SLA) or leaf area to leaf weight ratio. It is expressed in $m^2$ (leaf) $kg^{-1}$ (plant);

the leaf mean fraction (LMF) or leaf biomass to total plant biomass ratio. It is expressed in kg (leaf) $kg^{-1}$ (plant); or the net assimilation rate (NAR) or rate of increase in the weight of the plant per unit of leaf area. It is expressed in kg (plant) $m^{-2}$ (leaf) $day^{-1}$. The relative growth rate is equal to the product of LAR times NAR.

Other growth analysis parameters include:

the stem mass fraction (SMF) or stem biomass to total plant biomass ratio. It is expressed in kg (stem) $kg^{-1}$ (plant);

the root mass fraction (RMF) or root biomass to total plant biomass ratio. It is expressed in kg (root) $kg^{-1}$ (plant); and the dry matter (DM) or the dry plant weight to fresh plant weight ratio. It is expressed in kg (dry weight) $kg^{-1}$ (fresh weight).

The method of the invention can be applied to any type of photosynthetic organism, e.g., a plant, an alga, etc. Therefore, according to the present invention, when practically any photosynthetic organism is contacted with the growth factor of the invention, an increase in the biomass of said photosynthetic organism is obtained.

As indicated at the beginning of the present description, the growth factor of the invention is a peptide comprising the motif [Cys-$Xaa_1$-$Xaa_2$-$Xaa_3$-$Xaa_4$-Cys]. However, in a particular embodiment, the growth factor of the invention is a peptide comprising the motif [Cys-$Xaa_1$-$Xaa_2$-$Xaa_3$-$Xaa_4$-Cys], with the proviso that said peptide is not the peptide of SEQ ID NO: 4 or the peptide of SEQ ID NO: 6.

As the person skilled in the art will understand, said motif, optionally, will be flanked by other amino acid sequences forming part of the peptide identified as the growth factor of the invention.

Thus, in a particular embodiment, said peptide (growth factor of the invention) comprises the amino acid sequence

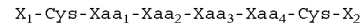

wherein:

$X_1$ represents the amino acid sequence of the amino-terminal end of the peptide, and $X_2$ represents the amino acid sequence of the carboxyl-terminal end of the peptide.

As it is used herein, the term "peptide" relates to a molecule formed by amino acid binding by means of peptide bonds, and it includes, for the sake of simplicity, peptides, polypeptides and proteins, although it is generally accepted that the term "protein" is applied to complete biological molecules with a stable conformation whereas the term "peptide" is generally reserved for short-chain amino acid oligomers which often lack a stable three-dimensional structure; likewise, the term "polypeptide" is typically reserved for any side chain of amino acids, regardless of their length (generally), which often lacks a defined conformation.

Although the length of the amino acid sequence of the amino-terminal end of the peptide ($X_1$) can vary within a broad range, in a particular embodiment $X_1$ has a length comprised between 1 and 250 amino acids, or even more typically between 1 and 175 amino acids, usually between 1 and 100 amino acids, more usually between 1 and 50 amino acids, even more usually between 2 and 40 amino acids, and yet even more usually between 5 and 35 amino acids.

Likewise, although the length of the amino acid sequence of the C-terminal end (or carboxyl terminus) of the peptide ($X_2$) can vary within a broad range, in a particular embodiment $X_2$ has a length comprised between 1 and 250 amino acids, or even more typically between 1 and 175 amino acids, usually between 1 and 100 amino acids, more usually between 1 and 50 amino acids, even more usually between 2 and 40 amino acids.

amino acids, has an intramolecular disulfide bridge [Cys-Cys] and has high homology with the calcitonin gene-related peptide. The precursor protein, the preproadrenomedullin (SEQ ID NO: 2) has a length of 185 amino acids (GenBank accession no. AAC60642.1) which, after being processed intracellularly, will give rise to a mature protein having 52 amino acids, which will be adrenomedullin. In a particular embodiment of the method of the invention, AM is human adrenomedullin defined by SEQ ID NO: 3. Without wishing to be bound by any theory, it is believed that the fact that human AM presents activity on plant tissues is due to the existence of a similar factor in plants or in the microorganisms associated with them.

SEQ ID NO: 2

(preproadrenomedullin)
MKLVSVALMY LGSLAFLGAD TARLDVASEF RKKWNKWALS RGKRELRMSS

SYPTGLADVK AGPAQTLIRP QDMKGASRSP EDSSPDAARI RVKR<u>YRQSMN</u>

<u>NFQGLRSFGC RFGTCTVQKL AHQIYQFTDK DKDNVAPRSK ISPQGY</u><u><u>GRRR</u></u>

<u><u>R</u></u><u>RSLPEAGPG RTLVSSKPQA HGAPAPPSGS APHFL</u>

[The amino acid sequence of the adrenomedullin is underlined and the
amino acid sequence of the motif GRRRR is twofold underlined and in
bold print]

SEQ ID NO: 3

(human adrenomedullin)
YRQSMNNFQGLRSFG<u>C</u>RFGT<u>C</u>TVQKLAHQIYQFTDKDKDNVAPRSKISPQGY-NH$_2$

[The characteristic motif of adrenomedullin (Cys-Xaa$_1$-Xaa$_2$-Xaa$_3$-Xaa$_4$-
Cys) is in bold print, where the two cysteines forming the disulfide
bridge are underlined]

In a particular embodiment, the amino acid sequence of the C-terminal end of the peptide ($X_2$) comprises the amino acid sequence GRRRR (SEQ ID NO: 7), which, in a further particular embodiment, is located at a distance of 10 to 50 amino acids from the last Cys of the sequence Cys-Xaa$_1$-Xaa$_2$-Xaa$_3$-Xaa$_4$-Cys, i.e., there are from 10 to 50 amino acids between the last amino acid (Cys) of said sequence and the first amino acid (G) of sequence GRRRR (SEQ ID NO: 7).

In a particular embodiment, the C-terminal end of $X_2$ is amidated.

Illustrative examples of peptides comprising said motif [Cys-Xaa$_1$-Xaa$_2$-Xaa$_3$-Xaa$_4$-Cys] include but are not limited to the adrenomedullin, the *Arabidopsis* proteins the amino acid sequences of which are shown in sequences SEQ ID NO: 4, SEQ ID NO: 5 and SEQ ID NO: 6, the *Oryza sativa* (rice) proteins the amino acid sequences of which are shown in SEQ ID NO: 8, SEQ ID NO: 9 and SEQ ID NO: 10, and the *Thalassiosira pseudonana* (diatom) protein the amino acid sequence of which is shown in sequence SEQ ID NO: 11.

Therefore, in a particular embodiment of the method of the invention the growth factor of the invention is selected from the group consisting of adrenomedullin, the peptides the amino acid sequences of which are shown in SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10 and SEQ ID NO: 11, and combinations thereof, which will be described in detail below.

Adrenomedullin

Adrenomedullin (AM) is a hypotensive peptide originally found in human pheochromocytoma which consists of 52

As the person skilled in the art will understand, any variant of SEQ ID NO: 3 with the capacity to increase the biomass of a photosynthetic organism is also included within the present invention.

As it is used herein, the term "variant of SEQ ID NO: 3" relates to any peptide the amino acid sequence of which can be obtained from SEQ ID NO: 3 by means of conservative amino acid changes and checking that the resulting variant has the capacity to increase the biomass of a photosynthetic organism by means of the measurement of any of the parameters mentioned above. The conservative amino acid substitutions relate to the interchangeability of residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having side chains containing an amide group consists of asparagine and glutamine; a group of amino acids having aromatic side chains consists of phenylalanine, tyrosine and tryptophan; a group of amino acids having basic side chains consists of lysine, arginine, and histidine; and a group of amino acids having sulfur-containing side chains consists of cysteine and methionine. The preferred conservative amino acid substitution groups are: valine-leucine-isoleucine, phenylalanine-tyrosine, lysine-arginine, alanine-valine, and asparagine-glutamine.

The functionally equivalent variants of adrenomedullin include polypeptides which are substantially homologous to native adrenomedullin [SEQ ID NO: 3]. As it is used herein, the expression "substantially homologous" relates to any of the amino acid sequences having a degree of identity with respect to the amino acid sequence shown in SEQ ID NO:

3 of at least 50%, advantageously at least 60%, preferably at least 70%, more preferably at least 85% and even more preferably at least 95%. The degree of identity between two peptides can be determined using computer algorithms and methods which are widely known by the persons skilled in the art. The identity between two amino acid sequences of two peptides is preferably determined using the BLASTP algorithm (BLAST Manual, Altschul, S. et al., NCBI NLM NIH Bethesda, Md. 20894, Altschul, S., et al., J., 1990, Mol. Biol. 215:403-410).

On the other hand, adrenomedullin has a characteristic motif (or identifying feature) in its amino acid sequence which is involved in the adrenomedullin receptor recognition, consisting of a 6 amino acid ring created by the disulfide bond between two cysteines [Cys-$Xaa_1$-$Xaa_2$-$Xaa_3$-$Xaa_4$-Cys]. Adrenomedullin additionally has an amidated carboxyl-terminal end ($CONH_2$) separated from the motif by about 20-40 amino acids. Any adrenomedullin variant having the Cys-$Xaa_1$-$Xaa_2$-$Xaa_3$-$Xaa_4$-Cys motif in its amino acid sequence will recognize the adrenomedullin receptor and trigger the processes which lead to an increase of the biomass of the photosynthetic organism. Thus, the present invention also contemplates those adrenomedullin variants with the capacity for increasing the biomass of a photosynthetic organism comprising said 6 amino acid ring created by the disulfide bond between two cysteines. The SEQ ID NO: 3 variants can additionally have an amidated carboxyl-terminal end.

Finally, fragments of adrenomedullin or of the variants thereof as previously defined are also included within the present invention provided they maintain the capacity to increase the biomass of a photosynthetic organism. Said capacity can be determined by means of the parameters mentioned in previous paragraphs.

*Arabidopsis* Proteins

Other particular embodiments of the growth factor of the invention include the *Arabidopsis* proteins described in SEQ ID NO: 4, SEQ ID NO: 5 and SEQ ID NO: 6.

```
The protein identified under sequence
                                          SEQ ID NO: 4
[MLDTLIGGIVGGIAGAIIGTVDGFARGIGICPDSYQSCTRTDCEEHKKK LPTNLSRNGGAAAVKAKENGRRRRQKDRE-NH2] is a protein of an unknown name with GenBank accession no.

NP_564910.
```

```
The protein identified under sequence
                                          SEQ ID NO: 5
[MDPKSCENSSDVKGQTSDSVSKKVLIEEEEDVKKPQQGKENDSRMAKDV

VSCSSNISAHVVHEEVADNVTAVSCNEAESDISKAKAKEFHTIDLSGVGE

RICRICHFGSDQSPEASGDDKSVSPELIEIGCKCKNELGLAHFHCAEAWF

KLRGNSVCEICGCTAKNVTVRLMEDWSGERDNTLDGRRRRGRGQSCCIFM

VFLLTILLLHWFFKKISGYYQNT-NH2] is a protein of the zinc finger family (C3HC4-type Ring finger) with GenBank accession no. NP_180967.
```

```
The protein identified under
                                          SEQ ID NO: 6
[MGDVILFIDDTKSKVRITRCRICHEEEEESFFEVPCACSGTVKFAHRNC

IQRWCNEKGNTTCEICLQVYKDGYTAVLKQSKLIEQEVTIRVNGRRRRRS

RRLVSIAESDISQCNSVADRGASFCRSLTFTLSVFLLMKHTFDVIYGTEE

YPFSVFTVLTLKAIGILLPMFIIIRTISTIQKTLRRRHQYPESEEEDRLS

SDDDDDLEEEDEEQQQHLA-NH2] is a protein called pitchoun 1 (PIT1) with GenBank accession no.

NP_567222.

[In all the cases, the characteristic motif of the
growth factor of the invention (Cys-Xaa1-Xaa2-
Xaa3-Xaa4-Cys) is in bold print, the two cysteines
forming the disulfide bridge are underlined and
the amino acid sequence of the motif GRRRR is
twofold underlined and in bold print]
```

As the person skilled in the art will understand, variants and fragments of said proteins also are included in the context of the present invention, provided they conserve the characteristic motif of the growth factor of the invention and when they are administered to a photosynthetic organism they increase the biomass thereof. The increase of the biomass of a photosynthetic organism can be ascertained by means of any of the parameters mentioned above, for example, by means of a plant biomass increase assay such as the one described in Example 1, or by means of an alga biomass increase assay such as the one described in Example 2. The term variant and its meaning in the context of the present invention have been defined in previous paragraphs.

*Oryza sativa* Proteins

The peptides comprising the motif [Cys-$Xaa_1$-$Xaa_2$-$Xaa_3$-$Xaa_4$-Cys] include, without limitation, the proteins of *Oryza sativa* (rice) whose amino acid sequences are shown in SEQ ID NO: 8, SEQ ID NO: 9 and SEQ ID NO: 10.

```
SEQ ID NO: 8:
MEAAPRDDKPARMNSEDDDGHRRWGSDGGEAMPRTTSPVRRCDAGGGGGVADSAWEEEGPTGEI

PARRMERPARHGGVPAKYGRRLDGEDDGVLVPGEVVATSASAQETRQRRPEAEQWRQRHCCRRG

CTSGGVRGKRRAGRGRGGDYDAGGGDGTAGRRADAAAGVAGFGRRRRRERRSATVWLGRSGRGK

TEGEVD*

SEQ ID NO: 9 (protein receptor-like protein kinase 2 precursor,
putative, expressed):
MHAACLCSTCCSCRPRCAARRPRRARRRRCSRGRTPCRARRRRRPASSGRGRRRRRSSRTRTPR

RGARGAAWRRRVGRRGGRRRGGAGVAGTLDALDLSSLPGLAALNLSLNSLTGSFPSNVSSPLLS
```

-continued
```
LRSIDLSSNNLSGPIPAALPALMPNLEHLNLSSNQFSGEIPASLAKLTKLQSVVLGSNLLHGGV

PPVIGNISGLRTLELSGNPLGGAIPTTLGKLRSLEHINVSLAGLESTIPDELSLCANLTVIGLA

GNKLTGKLPVALARLTRVREFNVSKNMLSGEVLPDYFTAWTNLEVFQADGNRFTGEIPTAITMA

SRLEFLSLATNNLSGAIPPVIGTLANLKLLDLAENKLAGAIPRTIGNLTSLETLRLYTNKLTGR

LPDELGDMAALQRLSVSSNMLEGELPAGLARLPRLVGLVAFDNLLSGAIPPEFGRNGQLSIVSM

ANNRFSGELPRGVCASAPRLRWLGLDDNQFSGTVPACYRNLTNLVRLRMARNKLAGDVSEILAS

HPDLYYLDLSGNSFDGELPEHWAQFKSLSFLHLSGNKIAGAIPASYGAMSLQDLDLSSNRLAGE

IPPELGSLPLTKLNLRRNALSGRVPATLGNAARMEMLDLSGNALDGGVPVELTKLAEMWYLNLS

SNNLSGEVPPLLGKMRSLTTLDLSGNPGLCGHDIAGLNSCSSNTTTGDGHSGKTRLVLAVTLSV

AAALLVSMVAVVCAVSRKARRAAVVVEKAETSASGGGGSSTAAAVQASIWSKDTTFSFGDILAA

TEHFNDAYCIGKGSFGTVYRADLGGGRAVAVKRLDASETGDACWGVSERSFENEVRALTRVRHR

NIVKLHGFCAMGGYMYLVYELAERGSLGAVLYGGGGGGGCRFDWPARMRAIRGVAHALAYLHHD

CSPPMIHRDVSVNNVLLDPDYEPRVSDFGTARFLVPGRSTCDSIAGSYGYMAPELAYMRVTTKC

DVYSFGVVAMEMLMGKYPGGLISSLQHSPQSLSAEGHDGSGGGGGEEASASASRRLLLKDVVDQ

RLDAPAGKLAGQVVFAFVVALSCVRTSPDARPTMRAVAQELAARRRPILDRPFEMIKIGDLTNS

HR*

SEQ ID NO: 10:
MSRRGTRRQRDGNGDRGAASSSSPSTSPSHGPAGGWASQIRCCGAWCGGRTSVAVMLGDGAPVL

LGRRRRRRPPSSLLLMLFFFFFFHVQNACMPCSLAC*
```

[In all the cases, the characteristic motif of the growth factor of the invention (Cys-Xaa$_1$-Xaa$_2$-Xaa$_3$-Xaa$_4$-Cys) is in bold print, the two cysteines forming the disulfide bridge are underlined and the amino acid sequence of the motif GRRRR is twofold underlined and in bold print]

*Thalassiosira pseudonana* (Diatom) Protein

```
SEQ ID NO: 11:
MAPALCGDLISTRRSFLALAWTLTTLLSFFSFVVAVFLAGRINQQYISMT

SGDYAEWYTHEYGNDFYDRLLEEGSGECCRYLEGGEEGGGGEQQREGEDH

DRQEGGSNDRNQLDAEFFQSLANANSRSLEFAGVYTTVLGIALSLYGSTV

VVGFMSLKGEYIPPCFSFRSMSMIEEEGEVGVEDADTGPRNLWGEKIHRG

VFLGCLVIFANLLLLCAVIFGELEVHDNYNNYDQQNNDNIFSYRIEKISS

VFAITCIVLACVYVLFAVIYLSCGGMLDDDNDTVQHNTGNWMDHSHSQFE

LSPRGNGRRRRRGRRDMPDKAEPLVSAVGGGITEIGCATRSDERAYVLDE

GCIDETT*
```

[The characteristic motif of the growth factor of the invention (Cys-Xaa$_1$-Xaa$_2$-Xaa$_3$-Xaa$_4$-Cys) is in bold print, the two cysteines forming the disulfide bridge are underlined and the amino acid sequence of the motif GRRRR is twofold underlined and in bold print]

In order for the growth factor of the invention to have the desired effect, i.e., increasing the biomass of a photosynthetic organism, it is necessary to contact said growth factor with said photosynthetic organism. In the state of the art there are a number of processes which allow administering active ingredients (in the present invention, the growth factor of the invention) to photosynthetic organism, specially plants. Likewise, the active ingredient will be formulated in a manner suited to the method of administration to be used.

Usually for its administration to photosynthetic organism, the growth factor of the invention will be part of a composition that can be used either in solid form or in liquid form, for example, in the form of a wettable powder or of an emulsifiable concentrate incorporating conventional diluents. Said compositions can be obtained in the traditional manner, for example, by mixing the growth factor of the invention with a diluent and optionally with other ingredients or constituents. In a particular embodiment, the photosynthetic organism is a plant and then the composition composition comprising the growth factor of the invention can be obtained, by conventional means, by mixing the growth factor of the invention with a diluent and optionally with other ingredients or constituents which are usually used in agricultural compositions and which are known by the person skilled in the art, such as, but not limited to, solvents, active agents or pH regulators, fertilizers, etc. In a particular embodiment, the growth factor of the invention is administered as an additive to supplement the nutritive solution fed to the plant in a hydroponic system or, in another particular embodiment, it is administered to the irrigation water of said plant.

The concentration of the growth factor of the invention in the composition can vary within a broad range, typically from at least $10^{-2}$ to $10^{-16}$ M, usually from at least $10^{-4}$ to $10^{-12}$ M, more usually from at least $10^{-6}$ to $10^{-11}$ M, still more usually from at least $10^{-8}$ to $10^{-10}$ M. Additional technical features of said composition are, for example, the agriculturally acceptable carriers that can be used, the additional components that can be incorporated, its presentation form, the process for obtaining it, etc.

In the sense used in this description, the term "agriculturally acceptable carrier" includes any substance or combination of substances that can be used in the agricultural sector, and it includes any agriculturally acceptable liquid or solid material that can be added and/or mixed with the growth factor of the invention in order to make it a simpler or improved application form, or with an applicable or desirable activation intensity.

The composition herein described can furthermore contain, if desired, other ingredients or constituents usually used in agricultural compositions, such as, but not limited to, solvents, active agents or pH regulators, fertilizers, etc., provided they all allow or do not jeopardize or compromise the capacity of the growth factor of the invention to increase the plant biomass of a plant. Said ingredients or constituents usually used in agricultural compositions are generally known by the persons skilled in the art.

The composition provided by this invention can be obtained by conventional methods generally based on the mixture of the different components of the composition in the suitable amounts.

As indicated above, the method of the invention can be used on any photosynthetic organism. In a particular embodiment, the method of the invention will be applied to those photosynthetic organisms in which an increase of the biomass is particularly desirable, such as, for example, plants and algae which can be industrially used in any kind of industry. Thus, in a particular embodiment, the photosynthetic organism is a plant, for example, a plant for use in the production of energy, e.g., renewable energies, for human or animal nutrition, wood species, ornamental plants, etc.

Examples of plants the biomass of which is used in the production of fuels or renewable energies include but are not limited to:

(i) plants for use in the production of electric energy: obtained mainly from fast-growing wood energy crops, such as poplar, willow, eucalyptus, locust, coniferous trees, acacia, banana tree, etc., and herbaceous plants, such as thistle, miscanthus, giant reed, euphorbia, prickly pear cacti, etc.; and (ii) plants for use in the production of biofuels: production of bioalcohols obtained from beet, corn, sweet sorghum, sugar cane, potato, topinambur, etc., and bio-oils obtained from rape seed, sunflower, soy, etc.

As the person skilled in the art will understand, it is also possible to use plant biomass in obtaining thermal energy and producing fuel gases. However, due to the characteristics of these processes (thermal energy consists of applying direct combustion systems to obtain heat, and the production of fuel gases consists of breaking down the biomass in a digester to obtain a gas), the biomass used in the production of said energy can come from any plant.

Examples of wood plants include but are not limited to pine, eucalyptus, cork oak, cedar, oak, holm oak, etc.

Illustrative non-limiting examples of ornamental plants of interest include plants belonging to the *Aeschynanthus; Canna; Columnea; Anemone; Azalea; Begonia; Calceolaria; Camelia; Dianthus; Freesia; Gerbera; Hibiscus; Hypoestes; Kalanchoe; Nicotiana; Pelargonium; Petunia; Primula; Ranunculus; Rhipsalidopsis; Rosa; Saintpaulia; Sinningia-gloxinia; Streptocarpus; Tigridia; Verbena;* or *Zinnia* genus. Other ornamental plants include orchids (Orchidaceae family) and ornamental shrubs, which include bay laurel (*Laurus nobilis*), honeysuckle (*Lonicera fragrantissima*), star *magnolia* (*Magnolia stellata*), hydrangea (*Hydrangea macrophylla*), Laburnum (*Laburnum×watereri*), Japanese rose or *kerria* (*Kerria japonica*), etc.

Illustrative non-limiting examples of plants used in human or animal nutrition include fruit trees, which include but are not limited to the cherry tree, plum tree, peach tree, apricot tree, olive tree, mango tree, pear tree, apple tree, loquat tree, quince tree, orange tree, lemon tree, fig tree, papaya tree, chestnut tree, oak tree, holm oak tree, kermes oak tree, hazelnut tree, almond tree, walnut tree, etc.; forage plants, which include but are not limited to legumes (for example, clovers, alfalfas, clitorias, arachis, leucaena, bellflowers, etc.), grasses (for example, rye grass, fescue, orchard grass, blue grama grass, rhodes grass, buffel grass, andropogons, brachiarias, Bermuda grass considered grazing grass, and elephant grass, merkeron, sugar cane, Taiwan grass and corn grass, which are harvesting grass, etc.), grains (for example, sorghum, wheat, rye, barley, etc.); plants for human consumption (lettuce, cabbage, spinach, Swiss chard, green beans, tomato plants, etc.), etc.

In another particular embodiment, the photosynthetic organism is an alga, for example, a microalga such as a microalga from the *Chlorella, Botryococcus, Nannochloropsis, Haematococcus, Neochloris* or *Tetraselmis* genus; further, illustrative, non-limitative, examples of algae within the context of the present invention include Aonori (*Enteromorpha intestinalis*) (several species of the green alga Monostroma) (Japan), Arame (*Eisenia bicyclis*), Badderlocks, jap. Sarumen (*Alaria esculenta*), Carola (*Callophyllis variegata*) (South America), Carrageen moss (*Mastocarpus stellatus*), Chlorella, Laminaria saccharina, Durvillea antarctica, Palmaria palmata, Euchema cottonii, Caulerpa lentillifera, Gulaman, Gulaman-Dagat (*Agardhiella tenera*), Hijiki o Hiziki (*Sargassum fusiforme*), Hondawara (*Sargassum enerve*), Chondrus crispus, Porphyra laciniata/Porphyra umbilicalis, Ulva lactuca, Sargassum echinocarpum, Saccharina japonica, Miru (*Codium* sp.), Mozuku (*Cladosiphon okamuranus*), Nori (several species of the red alga *Porphyra*), Oarweed (*Laminaria digitata*), Ogonori (several species of the red alga Gracilaria), *Fucus vesiculosus, Seatron* (*Nereocystis luetkeana*), Slack (*Porphyra purpurea,* syn. *Porphyra laciniata*), Arthrospira platensis, Arthrospira maxima, Thongweed (*Himanthalia elongata*), Tsunomato (several species of the red alga *Chondrus*), Wakame (*Undaria pinnatifida*), etc.

Gene Construct of the Invention

Another possibility contemplated by the present invention to achieve that the growth factor of the invention increases the biomass of a photosynthetic organism consists of inserting in the genome of said photosynthetic organism the nucleotide sequence encoding said growth factor such that when said nucleotide sequence is expressed it has the desired effect in the photosynthetic organism.

Therefore, in another aspect the invention relates to a gene construct, hereinafter, gene construct of the invention, comprising (a) a nucleic acid encoding a peptide which comprises
  (i) the amino acid sequence

[SEQ ID NO: 1]
Cys-Xaa$_1$-Xaa$_2$-Xaa$_3$-Xaa$_4$-Cys wherein
  Xaa$_1$, Xaa$_2$, Xaa$_3$ and Xaa$_4$ independently represent an amino acid, and
  (ii) the cysteine residues of the amino acid sequence shown in (i) form a disulfide bridge between them, and
(b) regulating elements for regulating its expression in a photosynthetic organism.

In a particular embodiment, said regulating elements are suitable for regulating the expression of the nucleic acid sequence encoding said peptide in an alga; said elements are known by those skilled in the art.

In another particular embodiment, said regulating elements are suitable for regulating the expression of the nucleic acid sequence encoding said peptide in a plant; said elements are also known by those skilled in the art.

In a particular embodiment, the regulating elements for regulating the expression of the nucleic acid sequence encoding said peptide are heterologous with respect to said nucleic acid sequence, i.e., in the event that said nucleic acid sequence encodes an *Arabidopsis* protein (e.g., SEQ ID NO: 4, SEQ ID NO: 5 or SEQ ID NO: 6), said nucleic acid sequence is under the control of regulating elements for regulating its expression in a plant different from the regulating elements that naturally regulate the expression of said *Arabidopsis* proteins in said plant, or in the event that said nucleic acid sequence encodes an *Oryza sativa* protein (e.g., SEQ ID NO: 8, SEQ ID NO: 9 or SEQ ID NO: 10),said nucleic acid sequence is under the control of regulating elements for regulating its expression in a plant different from the regulating elements that naturally regulate the expression of said *Oryza sativa* proteins in said plant; or in the event that said nucleic acid sequence encodes an *Thalassiosira pseudonana* (e.g., SEQ ID NO: 11), said nucleic acid sequence is under the control of regulating elements for regulating its expression in an alga different from the regulating elements that naturally regulate the expression of said *Thalassiosira* protein in said alga.

The amino acids Xaa$_1$, Xaa$_2$, Xaa$_3$ and Xaa$_4$ can be identical to or different from one another. In a particular embodiment, Xaa$_1$, Xaa$_2$, Xaa$_3$ and/or Xaa$_4$ is an amino acid different from Cys.

Therefore, in a particular embodiment, said gene construct of the invention comprises
(a) a nucleic acid encoding a peptide which comprises
  (i) the amino acid sequence

[SEQ ID NO: 1]
Cys-Xaa$_1$-Xaa$_2$-Xaa$_3$-Xaa$_4$-Cys wherein
  Xaa$_1$, Xaa$_2$, Xaa$_3$ and Xaa$_4$ independently represent an amino acid, and
  (ii) the cysteine residues of the amino acid sequence shown in (i) form a disulfide bridge between them, and
(b) regulating elements for regulating its expression in a photosynthetic organism,
with the proviso that when said nucleic acid sequence (a) encodes a protein selected from the group consisting of the proteins the amino acid sequences of which are shown in SEQ ID NO: 4, SEQ ID NO: 5 and SEQ ID NO: 6, said nucleic acid sequence (a) is under the control of regulating elements for regulating its expression in a plant different from the regulating elements that naturally regulate the expression of said proteins in *Arabidopsis* sp.; with the proviso that when said nucleic acid sequence (a) encodes a protein selected from the group consisting of the proteins the amino acid sequences of which are shown in SEQ ID NO: 8, SEQ ID NO: 9 and SEQ ID NO: 10, said nucleic acid sequence (a) is under the control of regulating elements for regulating its expression in a plant different from the regulating elements that naturally regulate the expression of said proteins in *Oryza sativa* sp.; and with the proviso that when said nucleic acid sequence (a) encodes a protein whose amino acid sequence is shown in SEQ ID NO: 11, said nucleic acid sequence (a) is under the control of regulating elements for regulating its expression in an alga different from the regulating elements that naturally regulate the expression of said proteins in *Thalassiosira pseudonana* (diatom).

In a particular embodiment of the gene construct of the invention, said peptide comprises the amino acid sequence X$_1$-Cys-Xaa$_1$-Xaa$_2$-Xaa$_3$-Xaa$_4$-Cys-X$_2$ wherein:
  X$_1$ represents the amino acid sequence of the amino-terminal end of the peptide, and
  X$_2$ represents the amino acid sequence of the carboxyl-terminal end of the peptide.

Although the length of the amino acid sequence of the amino-terminal end of the peptide (X$_1$) can vary within a broad range, in a particular embodiment X$_1$ has a length comprised between 1 and 250 amino acids, or even more typically between 1 and 175 amino acids, usually between 1 and 100 amino acids, more usually between 1 and 50 amino acids, even more usually between 2 and 40 amino acids, and yet even more usually between 5 and 35 amino acids.

Likewise, although the length of the amino acid sequence of the C-terminal end of the peptide (X$_2$) can vary within a broad range, in a particular embodiment, X$_2$ has a length comprised between 1 and 250 amino acids, or even more typically between 1 and 175 amino acids, usually between 1 and 100 amino acids, more usually between 1 and 50 amino acids, even more usually between 2 and 40 amino acids.

In a particular embodiment, the amino acid sequence of the C-terminal end of the peptide (X2) comprises the amino acid sequence GRRRR (SEQ ID NO: 7), which, in a further particular embodiment, is located at a distance of 10 to 50 amino acids from the last Cys of the sequence Cys-Xaa$_1$-Xaa$_2$-Xaa$_3$-Xaa$_4$-Cys.

In a particular embodiment, the C-terminal end of X$_2$ is amidated.

In another particular embodiment, said peptide is selected from the group consisting of adrenomedullin and the proteins the amino acid sequences of which are shown in sequences SEQ ID NO: 2, SEQ ID NO: 3, SEQ ID NO: 4, SEQ ID NO: 5, SEQ ID NO: 6, SEQ ID NO: 8, SEQ ID NO: 9, SEQ ID NO: 10, and SEQ ID NO: 11, as well as their functionally equivalent variants and fragments.

The gene construct of the invention can be obtained by means of using techniques well known in the state of the art [Sambrook et al., 2001. "Molecular cloning: a Laboratory Manual", 3$^{rd}$ ed., Cold Spring Harbor Laboratory Press, N.Y., Vol. 1-3]. Said gene construct of the invention incorporates, operatively bound thereto, regulating elements for regulating its expression in a photosynthetic organism. As it is used in this description, the expression "operatively bound" means that the nucleic acid encoding the growth factor of the invention [i.e., the peptide comprising the amino acid sequence Cys-Xaa$_1$-Xaa$_2$-Xaa$_3$-Xaa$_4$-Cys] is expressed in the correct reading frame under the control of the control regulating elements or the expression regulating sequences. The control regulating elements are sequences which control and regulate the transcription and, where appropriate, the translation of the protein, and include promoter sequences, encoding sequences for transcriptional regulators, ribosome-binding sequences (RBS) and/or transcription termination sequences.

The gene construct of the invention can be inserted in the genome of a photosynthetic organism cell, e.g., a plant cell or tissue, or an algal cell, by any suitable method to obtain transformed photosynthetic organisms. Said methods can involve, for example, the use of liposomes, electroporation, diffusion, particle bombardment, microinjection, gene guns, chemical compounds which increase free DNA uptake, for example, co-precipitation with calcium phosphate, viral vectors, etc.

Thus, in another aspect, the invention relates to a vector comprising the gene construct of the invention.

In a particular embodiment, said vector is a vector suitable for the transformation of algae; said vectors are known by the skilled person in the art (e.g., WO 2009149470 discloses methods and compositions for vector-transformed algal cells, wherein the vector comprises a Vcp promoter driving expression of an antibiotic resistance gene in an algal cell.

In another particular embodiment, said vector is a vector suitable for the transformation of plants; said vectors are also known by the skilled person in the art. In a more particular embodiment, vectors suitable for the transformation of plants include those derived from the *Agrobacterium tumefaciens* Ti plasmid, such as those described in EP 120516. In addition to the transformation vectors derived from the *Agrobacterium* Ti or Ri plasmids, alternative methods can be used to insert the gene construct in plant cells and tissues, such as, for example, but not limited to, by means of the vacuum infiltration protocol.

On the other hand, both the nucleic acid encoding a peptide which comprises (i) the amino acid sequence Cys-$Xaa_1$-$Xaa_2$-$Xaa_3$-$Xaa_4$-Cys [SEQ ID NO: 1] wherein $Xaa_1$, $Xaa_2$, $Xaa_3$ and $Xaa_4$ independently represent an amino acid, and (ii) the cysteine residues of the amino acid sequence shown in (i) form a disulfide bridge between them, [hereinafter, nucleic acid (a)] and the gene construct of the invention can also be incorporated in a vector which includes a prokaryotic replicon, i.e., a DNA sequence capable of directing autonomous replication and keeping the recombinant DNA molecule extrachromosomal when it is introduced in a prokaryotic host cell, such as a bacterium. Said replicons are known in the art. The vectors including a prokaryotic replicon furthermore generally include restriction sites for the insertion of the gene construct. These vectors are known of the state of the art, as is described, for example, in patent U.S. Pat. No. 6,268,552.

Likewise, the vectors can also include markers to check for the presence of heterologous DNA in the photosynthetic organisms, e.g., plant cells and/or tissues, or algal cells, which have been transformed. The genetic markers that allow selecting heterologous DNA in said photosynthetic organisms, e.g., plant cells, include the genes which confer resistance to antibiotics, for example, ampicillin, tetracycline, kanamycin, hygromycin, gentamicin, etc. The neomycin phosphotransferase gene has the advantage of being expressed both in eukaryotic and prokaryotic cells. The marker allows selecting the satisfactorily transformed photosynthetic organisms, e.g., plants, grown in a medium containing the corresponding antibiotic because they incorporate the suitable resistance gene.

The introduction of said nucleic acid (a) as well as the introduction of said gene construct to transform a photosynthetic organism, e.g., a plant cell or tissue, or an algal cell, and generate a transgenic photosynthetic organism, e.g., a transgenic plant or a transgenic alga, can be carried out, as has been mentioned above, by any means known in the state of the art, including but not limited to DNA transfer mediated by *A. tumefaciens*, preferably with an unarmed T-DNA vector, electroporation, direct DNA transfer, particle bombardment, etc. (for a revision on these topics, see, for example, Marta Izquierdo Rojo in "Ingenieria Genética y Transferencia Génica", 1999, Ediciones Pirámide, S. A, Madrid).

In another aspect, the invention relates to a host cell comprising said nucleic acid (a), a gene construct according to the invention or a vector as has been described above. Suitable host cells for containing a gene construct according to the invention or a vector as has been described above include but are not limited to prokaryotic cells, yeasts or eukaryotic cells, such as insect cells for example. As the person skilled in the art will understand, depending on the host cell to be transformed, the gene construct of the invention or the vector containing it can contain expression control sequences which can be functional in prokaryotic cells and organisms, for example, bacteria, etc., or functional in eukaryotic cells and organisms, for example, insect cells, mammal cells, etc.

In another aspect, the invention relates to a transgenic plant cell or alga comprising, integrated in its genome, said nucleic acid (a) or said gene construct of the invention. The techniques for culturing transformed plant cells and tissues, or algae, and regenerating transgenic plants or algae are well known in the state of the art, as are the cultivation and growth conditions of said plants or algae (see, for example, Marta Izquierdo (1999) cited above).

Thus, the transgenic plant obtained from a plant cell transformed with the gene construct of the invention, or the alga transformed with the gene construct of the invention, constitutes an additional inventive aspect of the present invention.

Use of the Growth Factor of the Invention

The capacity of the growth factor of the invention to increase the biomass of photosynthetic organism has applications in different industries depending on the photosynthetic organism. Thus, as indicated in previous inventive aspects, the growth factor of the invention can be used in increasing the biomass of algae or plants that are going to be used in the production of energy, in obtaining wood, in human or animal nutrition, or in the floriculture as a way to improve the appearance of ornamental plants.

The following examples illustrate the present invention and must not be considered as being limiting of the scope thereof.

EXAMPLE 1

Increase of Plant Biomass in Carrot and Tobacco Plants

Material and Methods

Carrot (*Daucus carota*) and tobacco (*Nicotiana tabacum*) calli were supplied by Carolina Biological Supply Company (Burlington, N.C., USA) and kept under sterile conditions in solid callus initiation medium for carrots or for tobacco respectively (also acquired from Carolina Biological). The specific composition thereof is available in the company's catalog.

A single callus was split into small fragments and these fragments were weighed under sterile conditions and seeded on fresh medium (solid callus initiation medium acquired from Carolina Biologicals) which contained different concentrations of the synthetic peptide human adrenomedullin (AM) (Phoenix Pharmaceuticals, Burlingame, Calif., USA). After 30 days of growth in the dark, the calli were weighed again and the growth rate was calculated as the quotient of the final weight divided by the initial weight.

The dry weight of each sample was calculated by subjecting the calli to an oven drying process at 250° C. for 24 hours.

Results

A growth increase in the calli following a dose-dependent response was observed both in the carrot and in the tobacco (FIG. 1). The most effective concentration of AM for stimulating cell growth was $10^{-10}$ M. A more moderate growth increase occurred at lower or higher concentrations. A 60% increase in the biomass when compared with the control was obtained at the optimal dose of AM.

In order to verify that this increase of mass was not due to an increase of tissue hydration, the dry weight of the tissue was measured and it was found that the differences were maintained, indicating that the increase of biomass corresponded to a net growth of the tissues involved.

The effect observed in the callus cells, consisting in an increase of growth (cell proliferation) in callus cells, is perfectly transferred to whole plants. Sometimes the increase in the cell proliferation will affect the organoleptic or physical properties of the plants. However, the biomass increase will be produced in the plants as it is produced in the callus cells.

EXAMPLE 2

Increase of Algal Biomass in Microalgae of the *Chlorella* genus

Material and Methods

Two identical cultures of *Chlorella* in Guillard F/2 medium [Guillard, R. R. L. 1975. Culture of phytoplankton for feeding marine invertebrates. pp 26-60. In Smith W. L. and Chanley M. H (Eds.) *Culture of Marine Invertebrate Animals*. Plenum Press, New York, USA.; Guillard, R. R. L. and Ryther, J. H. 1962. Studies of marine planktonic diatoms. I. *Cyclotella nana* Hustedt and *Detonula confervacea* Cleve. *Can. J. Microbiol.* 8: 229-239] (250 ml each) were prepared in two separate glass flasks. Then, 100 µl of said Guillard F/2 medium were added to a flask and 100 µl of said Guillard F/2 medium containing the synthetic peptide human adrenomedullin (AM) (Phoenix Pharmaceuticals, Burlingame, Calif., USA) in a sufficient amount to achieve a final concentration of $10^{-8}$ M to the other flask.

Air containing 5% $CO_2$ was continuously bubbled in the culture. The flasks were illuminated with a photoperiod of 12 hours light/12 hours dark.

Aliquots from the medium were periodically collected in order to assess the microalgae growth. Absorbance was measured at 680 nm with a Perkin Elmer Lambda 35 UV/Visible spectrofotometer.

Results

AM-treated microalgae grow up faster and reach the stationary phase sooner than the non-treated microalgae.

The invention claimed is:

1. A method for increasing the biomass of a photosynthetic organism which comprises cultivating said photosynthetic organism in the presence of an adrenomedullin, wherein the photosynthetic organism is a vascular plant or an alga, wherein the presence of adrenomedullin increases the biomass of the whole organism and wherein adrenomedullin is present in a concentration of $10^{-8}$ to $10^{-16}$ M.

2. The method according to claim 1, wherein said adrenomedullin is a human adrenomedullin.

3. The method according to claim 1, wherein said photosynthetic organism is a vascular plant and said adrenomedullin is administered as an additive to supplement the nutritive solution which feeds said plant in a hydroponic system, or it is administered to the irrigation water of said plant.

4. The method according to claim 1, wherein the photosynthetic organism is a vascular plant and said plant is selected from a plant used for the production of renewable energies, a plant for human or animal nutrition, a wood species, and an ornamental plant.

5. A gene construct for increasing the biomass of a photosynthetic organism comprising:
   (a) a nucleic acid encoding the peptide adrenomedullin, and
   (b) regulating elements for regulating its expression in a photosynthetic organism, wherein the photosynthetic organism is a vascular plant or an alga and wherein the adrenomedullin provided by the nucleic acid of the gene construct increases the biomass of the whole photosynthetic organism.

6. The gene construct according to claim 5, wherein said adrenomedullin is a human adrenomedullin.

7. A vector for increasing the biomass of a photosynthetic organism comprising a gene construct according to claim 5, wherein the photosynthetic organism is a vascular plant or an alga, and wherein the adrenomedullin provided by the nucleic acid of said gene construct increases the biomass of the whole organism.

8. A host cell for increasing the biomass of a photosynthetic organism comprising a gene construct according to claim 5 or a vector according to claim 7, wherein the photosynthetic organism is a vascular plant or an alga, and wherein the adrenomedullin provided by the nucleic acid of said gene construct or said vector increases the biomass of the whole organism.

9. A transgenic photosynthetic organism cell for increasing the biomass of a photosynthetic organism comprising, integrated in its genome, a gene construct according to claim 5, wherein the photosynthetic organism is a vascular plant or an alga, and wherein the adrenomedullin provided by the nucleic acid of said gene construct increases the biomass of the whole organism.

10. A transgenic photosynthetic organism for increasing the biomass of a photosynthetic organism comprising at least one transgenic photosynthetic organism cell according to claim 9, wherein the photosynthetic organism is a vascular plant or an alga, and wherein the adrenomedullin provided by the nucleic acid of the gene construct of said transgenic photosynthetic organism cell increases the biomass of the whole organism.

* * * * *

SEQUENCE LISTING

```
<160> NUMBER OF SEQ ID NOS: 11

<210> SEQ ID NO 1
<211> LENGTH: 6
<212> TYPE: PRT
<213> ORGANISM: Artificial sequence
<220> FEATURE:
<223> OTHER INFORMATION: Motif comprised within the growth factor of
      the invention
<220> FEATURE:
<221> NAME/KEY: misc_feature
<222> LOCATION: (2)..(5)
<223> OTHER INFORMATION: Xaa can be any naturally occurring amino acid

<400> SEQUENCE: 1

Cys Xaa Xaa Xaa Xaa Cys
1               5

<210> SEQ ID NO 2
<211> LENGTH: 185
<212> TYPE: PRT
<213> ORGANISM: Homo sapiens

<400> SEQUENCE: 2

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30
```

-continued

```
Lys Trp Asn Lys Trp Ala Leu Ser Arg Gly Lys Arg Glu Leu Arg Met
             35                  40                  45

Ser Ser Ser Tyr Pro Thr Gly Leu Ala Asp Val Lys Ala Gly Pro Ala
 50                  55                  60

Gln Thr Leu Ile Arg Pro Gln Asp Met Lys Gly Ala Ser Arg Ser Pro
 65                  70                  75                  80

Glu Asp Ser Ser Pro Asp Ala Ala Arg Ile Arg Val Lys Arg Tyr Arg
                 85                  90                  95

Gln Ser Met Asn Asn Phe Gln Gly Leu Arg Ser Phe Gly Cys Arg Phe
             100                 105                 110

Gly Thr Cys Thr Val Gln Lys Leu Ala His Gln Ile Tyr Gln Phe Thr
         115                 120                 125

Asp Lys Asp Lys Asp Asn Val Ala Pro Arg Ser Lys Ile Ser Pro Gln
130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Pro Ala Pro
                 165                 170                 175

Pro Ser Gly Ser Ala Pro His Phe Leu
            180                 185

<210> SEQ ID NO 3
<211> LENGTH: 52
<212> TYPE: PRT
<213> ORGANISM: Homo sapiens

<400> SEQUENCE: 3

Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
                 20                  25                  30

Phe Thr Asp Lys Asp Lys Asp Asn Val Ala Pro Arg Ser Lys Ile Ser
             35                  40                  45

Pro Gln Gly Tyr
 50

<210> SEQ ID NO 4
<211> LENGTH: 78
<212> TYPE: PRT
<213> ORGANISM: Arabidopsis thaliana

<400> SEQUENCE: 4

Met Leu Asp Thr Leu Ile Gly Gly Ile Val Gly Gly Ile Ala Gly Ala
 1               5                  10                  15

Ile Ile Gly Thr Val Asp Gly Phe Ala Arg Gly Ile Gly Ile Cys Pro
                 20                  25                  30

Asp Ser Tyr Gln Ser Cys Thr Arg Thr Asp Cys Glu Glu His Lys Lys
             35                  40                  45

Lys Leu Pro Thr Asn Leu Ser Arg Asn Gly Gly Ala Ala Val Lys
 50                  55                  60

Ala Lys Glu Asn Gly Arg Arg Arg Gln Lys Asp Arg Glu
 65                  70                  75

<210> SEQ ID NO 5
<211> LENGTH: 222
<212> TYPE: PRT
<213> ORGANISM: Arabidopsis thaliana
```

<400> SEQUENCE: 5

Met Asp Pro Lys Ser Cys Glu Asn Ser Ser Asp Val Lys Gly Gln Thr
1               5                   10                  15

Ser Asp Ser Val Ser Lys Lys Val Leu Ile Glu Glu Glu Glu Asp Val
            20                  25                  30

Lys Lys Pro Gln Gln Gly Lys Glu Asn Asp Ser Arg Met Ala Lys Asp
        35                  40                  45

Val Val Ser Cys Ser Ser Asn Ile Ser Ala His Val His Glu Glu
    50                  55                  60

Val Ala Asp Asn Val Thr Ala Val Ser Cys Asn Glu Ala Glu Ser Asp
65                  70                  75                  80

Ile Ser Lys Ala Lys Ala Lys Glu Phe His Thr Ile Asp Leu Ser Gly
                85                  90                  95

Val Gly Glu Arg Ile Cys Arg Ile Cys His Phe Gly Ser Asp Gln Ser
            100                 105                 110

Pro Glu Ala Ser Gly Asp Asp Lys Ser Val Ser Pro Glu Leu Ile Glu
        115                 120                 125

Ile Gly Cys Lys Cys Lys Asn Glu Leu Gly Leu Ala His Phe His Cys
    130                 135                 140

Ala Glu Ala Trp Phe Lys Leu Arg Gly Asn Ser Val Cys Glu Ile Cys
145                 150                 155                 160

Gly Cys Thr Ala Lys Asn Val Thr Val Arg Leu Met Glu Asp Trp Ser
                165                 170                 175

Gly Glu Arg Asp Asn Thr Leu Asp Gly Arg Arg Arg Gly Arg Gly
            180                 185                 190

Gln Ser Cys Cys Ile Phe Met Val Phe Leu Leu Thr Ile Leu Leu Leu
        195                 200                 205

His Trp Phe Phe Lys Lys Ile Ser Gly Tyr Tyr Gln Asn Thr
    210                 215                 220

<210> SEQ ID NO 6
<211> LENGTH: 218
<212> TYPE: PRT
<213> ORGANISM: Arabidopsis thaliana

<400> SEQUENCE: 6

Met Gly Asp Val Ile Leu Phe Ile Asp Asp Thr Lys Ser Lys Val Arg
1               5                   10                  15

Ile Thr Arg Cys Arg Ile Cys His Glu Glu Glu Glu Glu Ser Phe Phe
            20                  25                  30

Glu Val Pro Cys Ala Cys Ser Gly Thr Val Lys Phe Ala His Arg Asn
        35                  40                  45

Cys Ile Gln Arg Trp Cys Asn Glu Lys Gly Asn Thr Thr Cys Glu Ile
    50                  55                  60

Cys Leu Gln Val Tyr Lys Asp Gly Tyr Thr Ala Val Leu Lys Gln Ser
65                  70                  75                  80

Lys Leu Ile Glu Gln Glu Val Thr Ile Arg Val Asn Gly Arg Arg Arg
                85                  90                  95

Arg Arg Ser Arg Arg Leu Val Ser Ile Ala Glu Ser Asp Ile Ser Gln
            100                 105                 110

Cys Asn Ser Val Ala Asp Arg Gly Ala Ser Phe Cys Arg Ser Leu Thr
        115                 120                 125

Phe Thr Leu Ser Val Phe Leu Leu Met Lys His Thr Phe Asp Val Ile
    130                 135                 140

```
Tyr Gly Thr Glu Glu Tyr Pro Phe Ser Val Phe Thr Val Leu Thr Leu
145                 150                 155                 160

Lys Ala Ile Gly Ile Leu Leu Pro Met Phe Ile Ile Arg Thr Ile
            165                 170                 175

Ser Thr Ile Gln Lys Thr Leu Arg Arg Arg His Gln Tyr Pro Glu Ser
            180                 185                 190

Glu Glu Glu Asp Arg Leu Ser Ser Asp Asp Asp Asp Leu Glu Glu
            195                 200                 205

Glu Asp Glu Glu Gln Gln Gln His Leu Ala
        210                 215
```

```
<210> SEQ ID NO 7
<211> LENGTH: 5
<212> TYPE: PRT
<213> ORGANISM: Unknown
<220> FEATURE:
<223> OTHER INFORMATION: Motif

<400> SEQUENCE: 7

Gly Arg Arg Arg Arg
1               5

<210> SEQ ID NO 8
<211> LENGTH: 198
<212> TYPE: PRT
<213> ORGANISM: Oryza sativa

<400> SEQUENCE: 8

Met Glu Ala Ala Pro Arg Asp Asp Lys Pro Ala Arg Met Asn Ser Glu
1               5                   10                  15

Asp Asp Asp Gly His Arg Arg Trp Gly Ser Asp Gly Gly Glu Ala Met
            20                  25                  30

Pro Arg Thr Thr Ser Pro Val Arg Arg Cys Asp Ala Gly Gly Gly Gly
            35                  40                  45

Gly Val Ala Asp Ser Ala Trp Glu Glu Glu Gly Pro Thr Gly Glu Ile
    50                  55                  60

Pro Ala Arg Arg Met Glu Arg Pro Ala Arg His Gly Gly Val Pro Ala
65                  70                  75                  80

Lys Tyr Gly Arg Arg Leu Asp Gly Glu Asp Asp Gly Val Leu Val Pro
                85                  90                  95

Gly Glu Val Val Ala Thr Ser Ala Ser Ala Gln Glu Thr Arg Gln Arg
            100                 105                 110

Arg Pro Glu Ala Glu Gln Trp Arg Gln Arg His Cys Cys Arg Arg Gly
            115                 120                 125

Cys Thr Ser Gly Gly Val Arg Gly Lys Arg Arg Ala Gly Arg Gly Arg
130                 135                 140

Gly Gly Asp Tyr Asp Ala Gly Gly Gly Asp Gly Thr Ala Gly Arg Arg
145                 150                 155                 160

Ala Asp Ala Ala Ala Gly Val Ala Gly Phe Gly Arg Arg Arg Arg Arg
                165                 170                 175

Glu Arg Arg Ser Ala Thr Val Trp Leu Gly Arg Ser Gly Arg Gly Lys
            180                 185                 190

Thr Glu Gly Glu Val Asp
        195

<210> SEQ ID NO 9
<211> LENGTH: 1090
<212> TYPE: PRT
```

<213> ORGANISM: Oryza sativa

<400> SEQUENCE: 9

```
Met His Ala Ala Cys Leu Cys Ser Thr Cys Cys Ser Cys Arg Pro Arg
1               5                   10                  15

Cys Ala Ala Arg Pro Arg Arg Ala Arg Arg Arg Cys Ser Arg
            20                  25                  30

Gly Arg Thr Pro Cys Arg Ala Arg Arg Arg Arg Pro Ala Ser Ser
            35                  40                  45

Gly Arg Gly Arg Arg Arg Arg Ser Ser Arg Thr Arg Pro Arg
50                  55                  60

Arg Gly Ala Arg Gly Ala Ala Trp Arg Arg Val Gly Arg Arg Gly
65                  70                  75                  80

Gly Arg Arg Arg Gly Gly Ala Gly Val Ala Gly Thr Leu Asp Ala Leu
                85                  90                  95

Asp Leu Ser Ser Leu Pro Gly Leu Ala Ala Leu Asn Leu Ser Leu Asn
            100                 105                 110

Ser Leu Thr Gly Ser Phe Pro Ser Asn Val Ser Ser Pro Leu Leu Ser
            115                 120                 125

Leu Arg Ser Ile Asp Leu Ser Ser Asn Asn Leu Ser Gly Pro Ile Pro
    130                 135                 140

Ala Ala Leu Pro Ala Leu Met Pro Asn Leu Glu His Leu Asn Leu Ser
145                 150                 155                 160

Ser Asn Gln Phe Ser Gly Glu Ile Pro Ala Ser Leu Ala Lys Leu Thr
                165                 170                 175

Lys Leu Gln Ser Val Val Leu Gly Ser Asn Leu Leu His Gly Gly Val
            180                 185                 190

Pro Pro Val Ile Gly Asn Ile Ser Gly Leu Arg Thr Leu Glu Leu Ser
        195                 200                 205

Gly Asn Pro Leu Gly Gly Ala Ile Pro Thr Thr Leu Gly Lys Leu Arg
    210                 215                 220

Ser Leu Glu His Ile Asn Val Ser Leu Ala Gly Leu Glu Ser Thr Ile
225                 230                 235                 240

Pro Asp Glu Leu Ser Leu Cys Ala Asn Leu Thr Val Ile Gly Leu Ala
                245                 250                 255

Gly Asn Lys Leu Thr Gly Lys Leu Pro Val Ala Leu Ala Arg Leu Thr
            260                 265                 270

Arg Val Arg Glu Phe Asn Val Ser Lys Asn Met Leu Ser Gly Glu Val
        275                 280                 285

Leu Pro Asp Tyr Phe Thr Ala Trp Thr Asn Leu Glu Val Phe Gln Ala
    290                 295                 300

Asp Gly Asn Arg Phe Thr Gly Glu Ile Pro Thr Ala Ile Thr Met Ala
305                 310                 315                 320

Ser Arg Leu Glu Phe Leu Ser Leu Ala Thr Asn Asn Leu Ser Gly Ala
                325                 330                 335

Ile Pro Pro Val Ile Gly Thr Leu Ala Asn Leu Lys Leu Leu Asp Leu
            340                 345                 350

Ala Glu Asn Lys Leu Ala Gly Ala Ile Pro Arg Thr Ile Gly Asn Leu
        355                 360                 365

Thr Ser Leu Glu Thr Leu Arg Leu Tyr Thr Asn Lys Leu Thr Gly Arg
    370                 375                 380

Leu Pro Asp Glu Leu Gly Asp Met Ala Ala Leu Gln Arg Leu Ser Val
385                 390                 395                 400
```

```
Ser Ser Asn Met Leu Glu Gly Glu Leu Pro Ala Gly Leu Ala Arg Leu
                405                 410                 415

Pro Arg Leu Val Gly Leu Val Ala Phe Asp Asn Leu Leu Ser Gly Ala
            420                 425                 430

Ile Pro Pro Glu Phe Gly Arg Asn Gly Gln Leu Ser Ile Val Ser Met
        435                 440                 445

Ala Asn Asn Arg Phe Ser Gly Glu Leu Pro Arg Gly Val Cys Ala Ser
    450                 455                 460

Ala Pro Arg Leu Arg Trp Leu Gly Leu Asp Asp Asn Gln Phe Ser Gly
465                 470                 475                 480

Thr Val Pro Ala Cys Tyr Arg Asn Leu Thr Asn Leu Val Arg Leu Arg
                485                 490                 495

Met Ala Arg Asn Lys Leu Ala Gly Asp Val Ser Glu Ile Leu Ala Ser
            500                 505                 510

His Pro Asp Leu Tyr Tyr Leu Asp Leu Ser Gly Asn Ser Phe Asp Gly
        515                 520                 525

Glu Leu Pro Glu His Trp Ala Gln Phe Lys Ser Leu Ser Phe Leu His
    530                 535                 540

Leu Ser Gly Asn Lys Ile Ala Gly Ala Ile Pro Ala Ser Tyr Gly Ala
545                 550                 555                 560

Met Ser Leu Gln Asp Leu Asp Leu Ser Ser Asn Arg Leu Ala Gly Glu
                565                 570                 575

Ile Pro Pro Glu Leu Gly Ser Leu Pro Leu Thr Lys Leu Asn Leu Arg
            580                 585                 590

Arg Asn Ala Leu Ser Gly Arg Val Pro Ala Thr Leu Gly Asn Ala Ala
        595                 600                 605

Arg Met Glu Met Leu Asp Leu Ser Gly Asn Ala Leu Asp Gly Gly Val
    610                 615                 620

Pro Val Glu Leu Thr Lys Leu Ala Glu Met Trp Tyr Leu Asn Leu Ser
625                 630                 635                 640

Ser Asn Asn Leu Ser Gly Glu Val Pro Pro Leu Leu Gly Lys Met Arg
                645                 650                 655

Ser Leu Thr Thr Leu Asp Leu Ser Gly Asn Pro Gly Leu Cys Gly His
            660                 665                 670

Asp Ile Ala Gly Leu Asn Ser Cys Ser Ser Asn Thr Thr Thr Gly Asp
        675                 680                 685

Gly His Ser Gly Lys Thr Arg Leu Val Leu Ala Val Thr Leu Ser Val
    690                 695                 700

Ala Ala Ala Leu Leu Val Ser Met Val Ala Val Val Cys Ala Val Ser
705                 710                 715                 720

Arg Lys Ala Arg Arg Ala Ala Val Val Glu Lys Ala Glu Thr Ser
                725                 730                 735

Ala Ser Gly Gly Gly Gly Ser Ser Thr Ala Ala Ala Val Gln Ala Ser
            740                 745                 750

Ile Trp Ser Lys Asp Thr Thr Phe Ser Phe Gly Asp Ile Leu Ala Ala
        755                 760                 765

Thr Glu His Phe Asn Asp Ala Tyr Cys Ile Gly Lys Gly Ser Phe Gly
    770                 775                 780

Thr Val Tyr Arg Ala Asp Leu Gly Gly Gly Arg Ala Val Ala Val Lys
785                 790                 795                 800

Arg Leu Asp Ala Ser Glu Thr Gly Asp Ala Cys Trp Gly Val Ser Glu
                805                 810                 815

Arg Ser Phe Glu Asn Glu Val Arg Ala Leu Thr Arg Val Arg His Arg
```

```
                820             825             830
Asn Ile Val Lys Leu His Gly Phe Cys Ala Met Gly Gly Tyr Met Tyr
            835             840             845
Leu Val Tyr Glu Leu Ala Glu Arg Gly Ser Leu Gly Ala Val Leu Tyr
            850             855             860
Gly Gly Gly Gly Gly Gly Cys Arg Phe Asp Trp Pro Ala Arg Met
865             870             875             880
Arg Ala Ile Arg Gly Val Ala His Ala Leu Ala Tyr Leu His His Asp
                885             890             895
Cys Ser Pro Pro Met Ile His Arg Asp Val Ser Val Asn Asn Val Leu
            900             905             910
Leu Asp Pro Asp Tyr Glu Pro Arg Val Ser Asp Phe Gly Thr Ala Arg
            915             920             925
Phe Leu Val Pro Gly Arg Ser Thr Cys Asp Ser Ile Ala Gly Ser Tyr
            930             935             940
Gly Tyr Met Ala Pro Glu Leu Ala Tyr Met Arg Val Thr Thr Lys Cys
945             950             955             960
Asp Val Tyr Ser Phe Gly Val Val Ala Met Glu Met Leu Met Gly Lys
                965             970             975
Tyr Pro Gly Gly Leu Ile Ser Ser Leu Gln His Ser Pro Gln Ser Leu
            980             985             990
Ser Ala Glu Gly His Asp Gly Ser  Gly Gly Gly Gly  Glu Glu Ala
            995             1000             1005
Ser Ala  Ser Ala Ser Arg Arg  Leu Leu Leu Lys Asp  Val Val Asp
            1010             1015             1020
Gln Arg  Leu Asp Ala Pro Ala  Gly Lys Leu Ala Gly  Gln Val Val
            1025             1030             1035
Phe Ala  Phe Val Val Ala Leu  Ser Cys Val Arg Thr  Ser Pro Asp
            1040             1045             1050
Ala Arg  Pro Thr Met Arg Ala  Val Ala Gln Glu Leu  Ala Ala Arg
            1055             1060             1065
Arg Arg  Pro Ile Leu Asp Arg  Pro Phe Glu Met Ile  Lys Ile Gly
            1070             1075             1080
Asp Leu  Thr Asn Ser His Arg
            1085             1090

<210> SEQ ID NO 10
<211> LENGTH: 100
<212> TYPE: PRT
<213> ORGANISM: Oryza sativa

<400> SEQUENCE: 10

Met Ser Arg Arg Gly Thr Arg Arg Gln Arg Asp Gly Asn Gly Asp Arg
1               5               10              15
Gly Ala Ala Ser Ser Ser Ser Pro Ser Thr Ser Pro Ser His Gly Pro
            20              25              30
Ala Gly Gly Trp Ala Ser Gln Ile Arg Cys Cys Gly Ala Trp Cys Gly
            35              40              45
Gly Arg Thr Ser Val Ala Val Met Leu Gly Asp Gly Ala Pro Val Leu
            50              55              60
Leu Gly Arg Arg Arg Arg Arg Pro Pro Ser Ser Leu Leu Leu Met
65              70              75              80
Leu Phe Phe Phe Phe Phe His Val Gln Asn Ala Cys Met Pro Cys
            85              90              95
```

Ser Leu Ala Cys
        100

<210> SEQ ID NO 11
<211> LENGTH: 357
<212> TYPE: PRT
<213> ORGANISM: Thalassiosira pseudonana

<400> SEQUENCE: 11

Met Ala Pro Ala Leu Cys Gly Asp Leu Ile Ser Thr Arg Arg Ser Phe
1               5                   10                  15

Leu Ala Leu Ala Trp Thr Leu Thr Thr Leu Leu Ser Phe Phe Ser Phe
            20                  25                  30

Val Val Ala Val Phe Leu Ala Gly Arg Ile Asn Gln Gln Tyr Ile Ser
        35                  40                  45

Met Thr Ser Gly Asp Tyr Ala Glu Trp Tyr Thr His Glu Tyr Gly Asn
    50                  55                  60

Asp Phe Tyr Asp Arg Leu Leu Glu Glu Gly Ser Gly Glu Cys Cys Arg
65                  70                  75                  80

Tyr Leu Glu Gly Gly Glu Glu Gly Gly Gly Glu Gln Gln Arg Glu
                85                  90                  95

Gly Glu Asp Lys Asp Arg Gln Glu Gly Gly Ser Asn Asp Arg Asn Gln
            100                 105                 110

Leu Asp Ala Glu Phe Phe Gln Ser Leu Ala Asn Ala Asn Ser Arg Ser
        115                 120                 125

Leu Glu Gly Ala Phe Val Tyr Thr Thr Val Leu Gly Ile Ala Leu Ser
    130                 135                 140

Leu Tyr Gly Ser Thr Val Val Gly Phe Met Ser Leu Lys Gly Glu
145                 150                 155                 160

Tyr Ile Pro Pro Cys Phe Ser Phe Arg Ser Met Ser Met Ile Glu Glu
                165                 170                 175

Glu Gly Glu Val Gly Val Glu Asp Ala Asp Thr Gly Pro Arg Asn Leu
            180                 185                 190

Trp Gly Glu Lys Ile His Arg Gly Val Phe Leu Gly Cys Leu Val Ile
        195                 200                 205

Phe Ala Asn Leu Leu Leu Cys Ala Val Ile Phe Gly Glu Leu Glu
    210                 215                 220

Val His Asp Asn Tyr Asn Asn Tyr Asp Gln Gln Asn Asn Asp Asn Ile
225                 230                 235                 240

Phe Ser Tyr Arg Ile Glu Lys Ile Ser Ser Val Phe Ala Ile Thr Cys
                245                 250                 255

Ile Val Leu Ala Cys Val Tyr Val Leu Phe Ala Val Ile Tyr Leu Ser
            260                 265                 270

Cys Gly Gly Met Leu Asp Asp Asp Asn Asp Thr Val Gln His Asn Thr
        275                 280                 285

Gly Asn Trp Met Asp His Ser His Ser Gln Phe Glu Leu Ser Pro Arg
    290                 295                 300

Gly Asn Gly Arg Arg Arg Arg Gly Arg Arg Asp Met Pro Asp Lys
305                 310                 315                 320

Ala Glu Pro Leu Val Ser Ala Val Gly Gly Ile Thr Glu Ile Gly
                325                 330                 335

```
Cys Ala Thr Arg Ser Asp Glu Arg Ala Tyr Val Leu Asp Glu Gly Cys
            340                 345                 350
Ile Asp Glu Thr Thr
        355
```